(12) United States Patent
Wells

(10) Patent No.: US 10,328,253 B2
(45) Date of Patent: Jun. 25, 2019

(54) MEDICAL ELECTRICAL STIMULATION LEAD INCLUDING EXPANDABLE COILED FIXATION ELEMENT

(71) Applicant: Medtronic, Inc., Minneapolis, MN (US)

(72) Inventor: Patrick D. Wells, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/360,378

(22) PCT Filed: Nov. 29, 2012

(86) PCT No.: PCT/US2012/067059
§ 371 (c)(1),
(2) Date: May 23, 2014

(87) PCT Pub. No.: WO2013/082283
PCT Pub. Date: Jun. 6, 2013

(65) Prior Publication Data
US 2014/0296954 A1    Oct. 2, 2014

Related U.S. Application Data

(60) Provisional application No. 61/565,374, filed on Nov. 30, 2011.

(51) Int. Cl.
*A61N 1/05* (2006.01)

(52) U.S. Cl.
CPC ............ *A61N 1/05* (2013.01); *A61N 1/0558* (2013.01)

(58) Field of Classification Search
CPC . A61N 1/08; A61N 1/375; A61N 1/05; A61N 1/0558; A61N 1/059; A61N 1/057; A61N 1/36125; A61F 2/82; A61F 2/07; A61F 2/88; A61M 25/04; A61M 25/10; A61M 25/0043; A61M 5/14276; A61B 2018/00214; A61B 2018/00267; A61B 2018/0022; A61B 5/6882;
(Continued)

(56) References Cited

U.S. PATENT DOCUMENTS 6,136,021 A * 10/2000 Tockman ............... A61N 1/057
600/381
6,909,920 B2  6/2005 Lokhoff et al.
(Continued)

FOREIGN PATENT DOCUMENTS

WO    WO 00/56399    9/2000

OTHER PUBLICATIONS

PCT/US2012/067059: Search Report and Written Opinion dated Feb. 12, 2013.

*Primary Examiner* — Nadia A Mahmood
(74) *Attorney, Agent, or Firm* — Shumaker & Sieffert, P.A.

(57) ABSTRACT

A medical lead includes a coiled conductor portion that defines at least part of an outer surface of the lead and an expandable coiled fixation element that defines at least a part of the outer surface of the lead. The expandable coiled fixation element is configured to expand from a first dimension in a first state to a second dimension in a second state in a direction away from the coiled conductor portion. In some examples, the expandable coiled fixation element comprises a shape memory material.

33 Claims, 6 Drawing Sheets

(58) Field of Classification Search
CPC ...... A61B 17/12136; A61B 2017/0437; A61B 2017/0443; A61B 2017/0649; A61B 2017/00867; A61B 2018/00285; A61B 2562/0209; A61B 5/0031; A61B 5/0215; A61B 5/6846; A61B 5/6853; A61B 5/6858; A61B 5/686
See application file for complete search history.

(56) References Cited

U.S. PATENT DOCUMENTS

| | | | |
|---|---|---|---|
| 7,107,105 B2 * | 9/2006 | Bjorklund | A61N 1/056 607/126 |
| 7,763,034 B2 | 7/2010 | Siegel et al. | |
| 7,765,012 B2 | 7/2010 | Gerber | |
| 7,881,783 B2 * | 2/2011 | Bonde | A61N 1/0558 607/2 |
| 7,887,550 B2 | 2/2011 | Daglow et al. | |
| 8,060,206 B2 * | 11/2011 | Kieval | A61B 5/02028 607/17 |
| 2004/0059404 A1 | 3/2004 | Bjorklund et al. | |
| 2005/0096718 A1 | 5/2005 | Gerber et al. | |
| 2007/0255366 A1 | 11/2007 | Gerber et al. | |
| 2007/0255370 A1 | 11/2007 | Bonde et al. | |
| 2007/0255383 A1 | 11/2007 | Gerber et al. | |
| 2008/0103573 A1 | 5/2008 | Gerber | |
| 2008/0103576 A1 | 5/2008 | Gerber | |
| 2008/0132982 A1 | 6/2008 | Gerber | |
| 2008/0171934 A1 * | 7/2008 | Greenan | A61B 5/6857 600/411 |
| 2008/0312725 A1 | 12/2008 | Penner et al. | |
| 2009/0088838 A1 | 4/2009 | Shaolian et al. | |
| 2009/0234407 A1 * | 9/2009 | Hastings | A61N 1/0565 607/14 |
| 2009/0270935 A1 | 10/2009 | Zhao et al. | |
| 2010/0094376 A1 | 4/2010 | Penner et al. | |

* cited by examiner

MEDICAL ELECTRICAL STIMULATION LEAD INCLUDING EXPANDABLE COILED FIXATION ELEMENT

TECHNICAL FIELD

The disclosure relates to medical leads, and, in particular, fixation of medical leads.

BACKGROUND

Electrical stimulation systems may be used to deliver electrical stimulation therapy to patients to treat a variety of symptoms or conditions. Some electrical stimulation systems have been proposed to address symptoms or conditions such as chronic pain, tremor, movement disorders, psychological disorders, multiple sclerosis, spinal cord injury, cerebral palsy, amyotrophic lateral sclerosis, dystonia, torticollis, epilepsy, pelvic floor disorders, gastroparesis, muscle stimulation (e.g., functional electrical stimulation (FES) of muscles) or obesity. In some examples, an electrical stimulation system includes an electrical stimulator that delivers electrical stimulation signals to a target stimulation site within a patient via at least one electrode of one or more electrical stimulation leads.

The electrical stimulation lead may be implanted in a patient on a temporary or permanent basis such that at least one stimulation electrode is positioned proximate to a target stimulation site. The target stimulation site may be, for example, a nerve or other tissue site, such as a spinal cord, pelvic nerve, pudendal nerve, stomach, bladder, or within a brain or other organ of a patient, or within a muscle or muscle group of a patient.

SUMMARY

In general, the disclosure is directed to a medical electrical stimulation lead that includes at least one coiled conductor that defines at least part of an outer surface of the medical lead, and an expandable coiled fixation element that also defines at least part of the outer surface of the medical lead. In some examples, the expandable coiled fixation element is physically separate from the at least one coiled conductor. The expandable coiled fixation element defines a plurality of turns, and at least one of the turns is configured to expand away from the coiled conductor from a first dimension in a first state of the fixation element to a second dimension in a second state of the fixation element. When expanded, the at least one of the turns of the coiled fixation element is configured to engage with tissue of a patient to help fix a position of the lead relative to a target stimulation site. Also described herein are systems including the electrical stimulation lead, methods for implanting the medical lead, and methods of forming the coiled fixation element.

In one example, the disclosure is directed to a system comprising medical lead comprising a coiled conductor that defines at least part of an outer surface of the medical lead, an electrode electrically connected to the coiled conductor, and an expandable coiled fixation element that defines at least part of the outer surface of the medical lead. The expandable coiled fixation element defines a plurality of turns, and at least one of the turns is configured to expand away from the coiled conductor from a first dimension in a first state to a second dimension in a second state.

In another example, the disclosure is directed to a medical lead comprising means for conducting electrical stimulation signals, wherein the means for conducting electrical stimulation signals comprises a coiled portion defining at least part of an outer surface of the medical lead, means for generating electrical stimulation therapy, wherein the means for generating electrical stimulation therapy is electrically connected to the means for conducting electrical stimulation signals, and means for fixing the means for conducting electrical stimulation signals to tissue of a patient, the means for fixing being coiled and defining at least part of the outer surface of the medical lead. The means for fixing defines a plurality of turns and at least one of the turns is configured to expand away from the coiled portion of the means for conducting from a first dimension in a first state to a second dimension in a second state.

In another example, the disclosure is directed to a method comprising implanting a medical lead in a patient, the medical lead comprising a coiled conductor that defines at least part of an outer surface of the medical lead, an electrode electrically connected to the coiled conductor, and an expandable coiled fixation element that defines at least part of the outer surface of the medical lead, wherein the expandable coiled fixation element defines a plurality of turns, and at least one of the turns is configured to expand away from the coiled conductor from a first dimension in a first state to a second dimension in a second state. The method further comprises applying thermal energy to the expandable coiled fixation element via a thermal energy source to cause the expandable coiled fixation element to expand away from the coiled conductor.

In another example, the disclosure is directed to a method comprising coiling a conductor to define a coiled conductor portion that defines at least part of an outer surface of a medical lead, and coiling an elongated member to define an expandable coiled fixation element that defines at least part of the outer surface of the medical lead, wherein the expandable coiled fixation element is configured to expand from a first dimension in a first state to a second dimension in a second state.

The details of one or more examples are set forth in the accompanying drawings and the description below. Other features, objects, and advantages will be apparent from the description and drawings, and from the claims.

DETAILED DESCRIPTION

Figure 1:
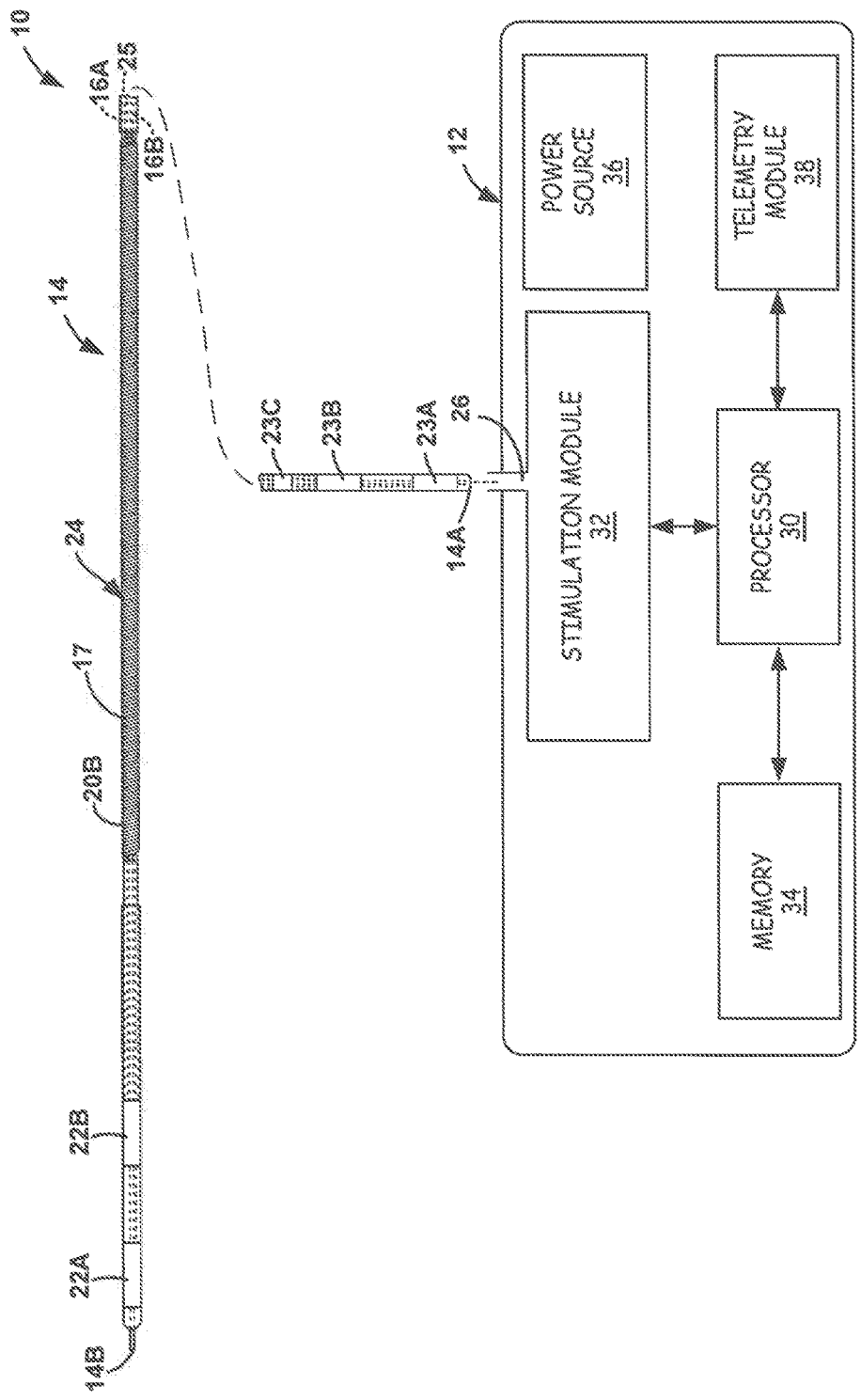
FIG. 1 is a conceptual illustration of an example therapy system that includes an electrical stimulator and an electrical stimulation lead that includes an expandable coiled fixation element, where expandable turns of the fixation element are in a first state.

In some electrical stimulation applications, it may be desirable to minimize migration of a medical electrical stimulation lead (also referred to herein as a "lead," a "medical lead," and a "stimulation lead") following implantation in a patient at a target stimulation site. For example, it may be desirable for one or more electrodes of the lead to remain proximate to the target stimulation site in order to provide adequate and reliable stimulation of the target stimulation site. Movement of stimulation electrodes of a lead from a target stimulation site may reduce electrical coupling between the electrode and the target stimulation site, possibly undermining therapeutic efficacy of the electrical stimulation therapy. In examples described herein, a lead includes an expandable coiled fixation element that is configured to expand from a first dimension (e.g., a first outer profile) in a first state of the fixation element to a second dimension (e.g., a second outer profile) in a second state of the fixation element to engage with tissue of a patient and help minimize lead migration following implantation of the lead in the patient, e.g., such that the one or more electrodes are positioned to deliver electrical stimulation signals to the target stimulation site. The coiled fixation element may be at least partially retractable, such as by stretching the coiled conductors to elongate the coiled fixation element, as discussed in further detail below, or by applying a force to the expanded fixation element (e.g., via a sheath that surrounds the coiled fixation element).

The expandable coiled fixation element may help ensure the electrodes of the lead deliver electrical stimulation to the target stimulation site as intended, which may be particularly useful if the lead is being used to test electrical stimulation therapy on the patient. Electrical stimulation therapy may be tested on a patient in order to determine whether the patient is responsive to electrical stimulation therapy, whether the patient is a candidate for successful long-term electrical stimulation therapy or to determine if electrical stimulation delivered with particular stimulation parameter values provides efficacious therapy to the patient. In some applications, the expandable coiled fixation element is configured to fix the lead such that the electrodes of the lead remain substantially co-located with a target stimulation site, e.g., substantially fixed to surrounding tissue, in order to help ensure the target tissue site is being stimulated, as opposed to a non-target tissue site. In addition, in some examples, fixing the lead may help maintain a minimum distance between the electrode and a nerve in order to help prevent inflammation to the nerve from the electrical stimulation.

The stimulation lead may be, for example, a test electrical stimulation lead (also referred to herein as a "test lead" or a "trial lead") in which an outer surface of the lead is at least partially defined by at least one coiled conductor that is configured to transmit electrical stimulation signals from an electrical stimulator at a proximal end of the conductor to an electrode at a distal portion of the conductor. Each coiled conductor may comprise example, an electrically conductive member surrounded by electrical insulation. In some examples, the electrical insulation defines at least a portion of the outer surface of the lead.

A test lead may be used to deliver electrical stimulation therapy to a patient on a trial basis, e.g., prior to surgical implantation of a fully implantable electrical stimulation lead that is used for chronic stimulation delivery. In some examples, the test lead is a percutaneous medical lead that is not intended to be fully implanted in the patient. Instead, a distal portion of the test lead may be implanted in the patient and a proximal portion of the lead may be external to the patient and electrically connected to an electrical stimulator. The distal portion of the lead may be implanted in the patient for the duration of a test period, in which electrical stimulation is delivered to the patient via the one or more electrodes of the test lead. In other examples, the test lead may be fully implanted in the patient (e.g., the entire length of the lead from the proximal end to the distal end may be implanted in the patient).

While the entire test lead may not be implanted in the patient, at least a portion of the lead including the one or more electrodes may be implanted in the patient. A test lead may be simplified relative to a lead intended for long-term implantation in a patient (also referred to as a "chronic lead") and may include a smaller profile (e.g., a smaller outer diameter or other perimeter), such that the test lead may be less invasive than the chronic lead. For example, as discussed in further detail below, the test lead may not include an outer jacket that encloses the conductor (coiled or uncoiled) and defines a smooth outer surface of the lead. The test lead may also be referred to as a temporary electrical stimulation lead or, when it is used to evaluate peripheral nerve stimulation, a "peripheral nerve evaluation lead," or when it is used to evaluate percutaneous nerve stimulation, a "percutaneous nerve evaluation lead."

Testing electrical stimulation therapy on a patient with a smaller profile test lead may be advantageous in some examples. For example, the smaller profile test lead may enable the test lead to be implanted (fully or partially) in the patient in a clinic, non-hospital setting, rather than in a hospital setting, which may be less intimidating to a patient and may also be more cost efficient. For example, a relatively small needle (e.g., an 18-20 gauge needle) may be used to implant some example test leads described herein, which may be used outside of a hospital setting. In addition, for some patients, the non-hospital setting procedure and the smaller size of the test lead may be less of an obstacle to the testing of the electrical stimulation therapy than a procedure that is required to be performed in a hospital and/or a procedure that requires the implantation of a relatively large lead.

Figure 2A:
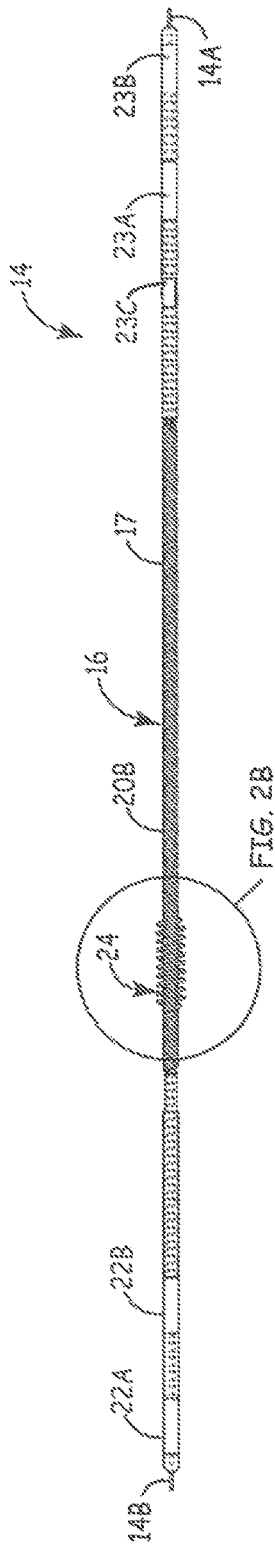
FIGS. 2A and 2B are conceptual illustrations of an example electrical stimulation lead that includes an expandable coiled fixation element, where at least some of the turns of the expandable coiled fixation element are in a second, expanded state.
Figure 2B:
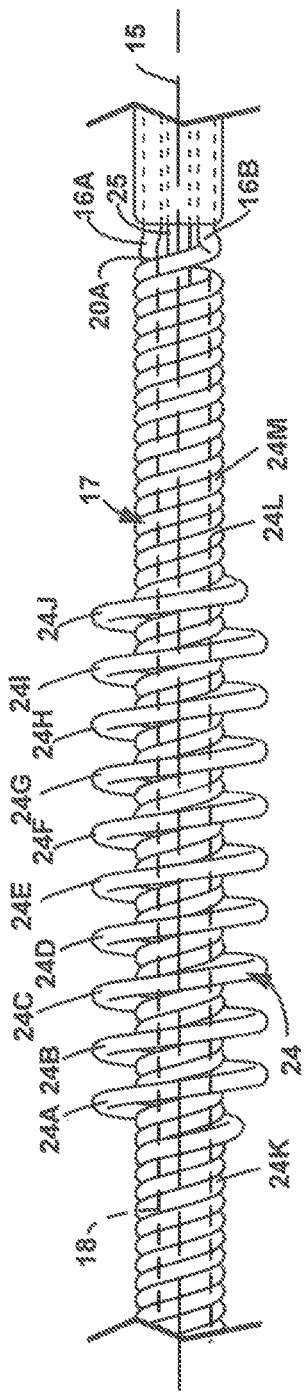

FIG. 1 is a conceptual diagram illustrating an example therapy system 10 that includes electrical stimulator 12 electrically connected to electrical stimulation lead 14. In the example shown in FIG. 1, lead 14 includes two conductors 16A, 16B, which are at least partially coiled around core 18 (shown in phantom lines in FIG. 2B), and electrodes 22A, 22B (collectively referred to as "electrodes 22"). Lead 14 further includes coiled fixation element 24 (also shown in FIGS. 2A and 2B) that is coiled with conductors 16 (collectively referred to as "conductors 16"). Lead 14 is separated into two segments in FIG. 1 for ease of illustration; the two segments may ordinarily be connected to each other, and the alignment of the segments is illustrated by an assembly line. FIGS. 2A and 2B further illustrate lead 14 and coiled fixation element 24, and are also referred to below in the description of lead 14.

In some examples, electrical stimulator 12 is configured to be implanted in a patient. In other examples, electrical stimulator 12 is configured to be carried external to a patient. For example, electrical stimulator 12 may be an external trial stimulator that is used to determine whether electrical stimulation therapy provides efficacious therapy to the patient, to determine whether the patient is a candidate for long-term electrical stimulation therapy, or to select one or more electrical stimulation parameters for long term therapy for the patient.

Electrical stimulator 12 is configured to generate and deliver a programmable stimulation signal (e.g., in the form of electrical pulses or a continuous time signal) that is delivered to a target stimulation site within a patient by lead 14, and more particularly, via electrodes 22 of lead 14. In some examples, electrical stimulator 12 may also be referred to as a signal generator or a neurostimulator. In some examples, electrical stimulator 12 may also include a sensing module that is configured to sense one or more physiological parameters of the patient via one or more electrodes 22 or a separate set of electrodes. Although one lead 14 is shown in FIG. 1, in other examples, electrical stimulator 12 may be coupled to two or more leads, e.g., to support delivery of electrical stimulation to multiple target stimulation sites within a patient, such as in the case of bilateral stimulation.

Lead 14 is configured to deliver electrical stimulation signals generated by electrical stimulator 14 to tissue of a patient proximate the one or more electrodes 22. Proximal end 14A of lead 14 may be both electrically and mechanically coupled to electrical stimulator 12 either directly or indirectly (e.g., via a lead extension). In some examples, the entire lead 14, from proximal end 14A to distal end 14B, may be configured to be implanted in a patient. In other examples, only a portion of lead 14 including distal end 14 and electrodes 22 is configured to be implanted in a patient. Lead 14 may be flexible in some examples, which may enable lead 14 to accommodate a plurality of different implantation sites within a patient, as well as decrease the irritation to adjacent tissue.

In the example shown in FIG. 1, lead 14 includes conductors 16A and 16B that are each at least partially coiled around core 18 to define coiled portion 17. In one example, only a portion of each of the conductors 16A, 16B is coiled, such that coiled portion 17 is only on a segment of lead 14, and a proximal portion of the respective conductor 16A, 16B adjacent proximal end 14A of lead 14 is not coiled, as shown in FIG. 1. In other examples, the proximal portion of each of the conductors 16A, 16B may be at least partially coiled, and, in some examples, the entire length of conductors 16A, 16B may be coiled from end to end.

Conductors 16A, 16B are configured to deliver electrical stimulation signals from electrical stimulator 12 to electrodes 22A, 22B, respectively. Conductors 16A, 16B each include an electrically conductive member surrounded by an electrically insulative material. The electrically conductive member can be formed from, for example, a stainless steel, such as MP35N alloy. The electrically insulative material may be any suitable biocompatible electrically insulative material, such as ethylene tetrafluoroethylene (ETFE), polytetrafluoroethylene (PTFE), silicone rubber, polyurethane, fluoropolymer, other suitable polymers, and the like. In the example shown in FIG. 1, electrodes 22A, 22B are defined by removing part of the electrically insulative material from each conductor 16A, 16B, respectively, thereby exposing the electrically conductive member, and mechanically and electrically connecting electrically conductive collar to the exposed electrically conductive members of the conductors 16. The electrically conductive collars may define the outer surface of electrodes 22 that contact tissue of a patient when distal end 14B of lead 14 is implanted in the patient, in other examples, electrodes 22 of lead 14 may be defined by, for example, uninsulated portions of the electrically conductive members of conductors 16. In this example, the exposed electrically conductive members of conductors 16 may define the outer surface of electrodes 22 that contact tissue of a patient when distal end 14B of lead 14 is implanted in the patient.

In the example shown in FIG. 1, electrodes 22 are immediately adjacent to distal end 14B of lead 14 and are positioned along a longitudinal outer surface of lead 14 (e.g., in contrast to a tip electrode that is at a distal tip of lead 14). In other examples, electrodes 22 can have other positions along lead 14, such as closer to middle portion of lead 14 (e.g., midway between proximal and distal ends 14A, 14B, respectively). In addition, while two electrodes 22A, 22B are shown in FIG. 1, in other examples, lead 14 may include any suitable number of electrodes, with or without electrically conductive collars. For example, lead 14 may include more than two conductors that define one or more respective electrodes, where the conductors are at least partially coiled (e.g., coaxially coiled and/or coiled together), and each conductor may define at least one respective electrode. As another example, lead 14 may include a single conductor that defines one electrode, which may be used to test unipolar electrical stimulation therapy. In the case of a unipolar stimulation lead with a single electrode (or multiple electrodes of a single polarity), the return path for the stimulation may be through the body of the patient, e.g., to an external ground pad or the like.

Lead 14 further includes electrical contacts 23A, 239, 23C (collectively referred to as "electrical contacts 23") near proximal end 14A of lead 14. Electrical contacts 23A, 239 are configured to electrically connect conductors 16A, 16B, respectively, to electrical stimulator 12, and, in particular, stimulation module 32 of electrical stimulator 12. Electrical contact 23 is configured to electrically connect expandable coiled fixation element 24 to electrical stimulator 12, and, in particular, stimulation module 32 of electrical stimulator 12. In the example shown in FIG. 1, electrical contacts 23A, 23B are defined by removing part of the electrically insulative material from each conductor 16A, 16B, thereby exposing the electrically conductive member. In some examples, an electrically conductive collar is mechanically and electrically connected to the exposed electrically conductive members of the conductors 16. The electrically conductive collars may define the outer surface of electrical contacts 23A, 23B that contact respective electrical contacts of electrical stimulator 12 when proximal end 14A of lead 14 is introduced in opening 26 defined by electrical stimulator 12 (e.g., opening 26 in a header of electrical stimulator 12). Electrical contact 23C may be defined by an outer surface of elongated member 25 (described in further detail below) or an electrically conductive collar electrically and mechanically connected to elongated member 25 that is introduced in opening 26 of electrical stimulator 12.

In FIG. 1, a proximal portion of lead 14 including proximal end 14A is illustrated as being aligned with proximal end opening 26 defined by electrical stimulator 16. Electrical contacts that are electrically connected to stimulation module 32 may be positioned within opening 26, such that when proximal end 14A of lead 14 is introduced in opening 26 and electrical contacts 23 contact respective electrical contacts in opening 26, electrical contacts 23 electrically connect stimulation module 32 to electrodes and expandable fixation element 24.

Coiled portion 17 (also referred to as a "coiled conductor portion") of lead 14 is defined by a plurality of turns (at least two turns) of conductors 16, and defines inner surface 20A (FIG. 2B) and outer surface 20B. As noted above, each conductor 16A, 16B may have an electrically insulative outer layer (e.g., a sheath, coating or the like), which may electrically insulated conductors 16 from each other. In some examples, at least some of the turns of conductors 16 are not mechanically connected to each other, such that the turns may move relative to each other. That is, the distance between adjacent turns may increase or decrease depending on the force applied to the ends of coiled portion 17, such that coiled portion 17 of conductor 16 can increase and decrease in length $L_C$, which is measured in a direction substantially parallel to a longitudinal axis of coiled portion 17. In some examples, increasing a length of coiled portion 17 may decrease the radius of curvature of the turns. As discussed in further detail below, this feature of lead 14 may aid in explanation of lead 14 from a patient by, for example, decreasing the extent to which expandable fixation element 24 extends away from outer surface 20B of coiled conductor 17 when elongated.

In some examples, none of the turns of coiled portion 17 are mechanically connected to each other. In other examples, some of the adjacent turns of coiled portion 17 are mechanically connected to each other, e.g., adhered or welded together. For example, the last two or three turns at either end of coiled portion 17 may be mechanically connected to each other.

In examples in which at least some of the adjacent turns of coiled portion 17 of conductor 16 are movable relative to each other, the coiled configuration of portion 17 may help accommodate axial forces placed on lead 14, e.g., help absorb the axial forces to help prevent migration of lead 14 (e.g., distal end 14B of lead 14). The axial forces may be applied, for example, in a direction substantially parallel to longitudinal axis 15 (FIG. 2B) of lead 14, such as from tugging or pulling on a proximal end 14A of lead 14. For example, when lead 14 is implanted in a patient and mechanically connected to electrical stimulator 12, relative movement between lead 14 and the stimulator 12 may generate axial forces that pull on lead 14. As another example, when lead 14 is implanted such that distal end 14B is implanted in the patient and proximal end 14A is carried external to the patient, forces applied to proximal end 14A, or anywhere along a length of lead 14, from ordinary activities of the patient may generate axial forces that pull on lead 14. Because coiled portion 17 may stretch and compress, coiled portion 17 may accommodate some relative movement between distal end 14B of lead 14 and proximal end 14A of lead 14.

Lead 14 may be, for example, a test lead in which an outer surface of lead 14 is at least partially defined by coiled conductors 16. In the example shown in FIG. 1, conductors 16 define an outer surface of lead 14 that contacts tissue of the patient when lead 14 is at least partially implanted in the patient. For example, in the example shown in FIG. 1, at least a portion of outer surface 20B of coiled portion 17 of conductors 16 is configured to directly contact tissue of the patient when lead 14 is at least partially implanted in the patient. In some examples, the entire outer surface 20B of coiled portion 17 of conductors 16 is configured to directly contact tissue of the patient when lead 14 is at least partially implanted in the patient.

In contrast to some leads configured for chronic implantation (e.g., long-term, non-temporary implantation, such as on the order of years) in a patient, lead 14 does not include an outer jacket (e.g., an outer electrically insulative jacket) in which conductors 16 of lead 14 are positioned, where the outer jacket defines an outer surface of the lead. That is, in the example shown in FIG. 1, an outer jacket is not positioned between coiled portion 17 of conductors 16 and tissue of the patient when lead 14 is implanted in the patient. Rather, at least a portion of the outer surface of lead 14 is defined by coiled portion 17 of conductors 16, such that coiled conductors 16 contact tissue of the patient when lead 14 is implanted in the patient. While conductors 16 each include an electrically conductive member surrounded by an electrically insulative material, at least a portion of coiled portion 17 of conductors 16 is not disposed within an outer jacket that is separate from the electrical insulative material of conductors 16. Conductors 16 may each be electrically insulated along their respective lengths, but no additional electrical insulation may be provided around that portion (or entire) coiled portion 17 of conductors 16 by a physically separate outer jacket. In some examples, no portion of conductors 16 is disposed within a common outer jacket that encloses coiled portion 17. The absence of an outer jacket or the like in which at least coiled portion 17 conductors 16 is placed may help decrease the profile of lead 14, e.g., by decreasing the total outer perimeter (e.g., an outer profile or outer diameter) of lead 14, which may help decrease the invasiveness of lead 14 when at least the portion of lead 14 including a part of coiled portion 17 of conductor 16 is implanted in a patient. In addition, an absence of the outer jacket may also help increase the ease with which lead 14 can be extended, e.g., to retract coiled fixation element 24 back from the second dimension to the first dimension.

As discussed above, conductors 16 are wrapped around core 18 to define coiled conductor portion 17. Core 18 is configured to increase the structural rigidity and stiffness of the section of lead 14 including the coiled portion 17. Increasing the structural rigidity and stiffness of the coiled portion 17 of conductor 16 may increase the ease with which lead 14 may be manipulated by a clinician, e.g., as distal end 14B of lead 14 is being guided to a target stimulation site within a patient. In some examples, core 18 may be formed from a material that is more structurally rigid than coiled portion 17 of conductor 16. Accordingly, in these examples, coiled portion 17 of conductor 16 may adopt the curvature or other shape of core 18 when core 18 is disposed within coiled portion 17 of conductor 16. In one example, core 18 is substantially cylindrical and has a substantially circular cross-section (e.g., measured in a direction substantially perpendicular to the longitudinal axis of core 18).

In some examples, core 18 is formed from a biocompatible material, such as a metal (e.g., a shape memory metal such as Nitinol), a polymer, and the like. For example, core 18 may be a metal stylet. In some examples, the configuration of core 18 (e.g., the size and material) is selected such that lead 14 can be manipulated (e.g., to navigate and steer lead 14 through tissue) from its proximal end by a clinician as the clinician implants lead 14 in a patient. For example, a thickness and material of core 18 can be selected to define a self-supporting core 18. However, a self-supporting core 18 is not present in all examples. Rather, the positioning of core 18 within the space defined by the inner surface 20A defined by coiled portion 17 of conductor 16 may be sufficient to increase the rigidity and stiffness of the section of lead 14 including the coiled portion 17. Core 18 may occupy a part of or the entire space defined by the inner surface 20A (FIGS. 2A and 2B) defined by coiled portion 17, such that core 18 engages with coiled portion 17 of conductor 18 as portion 17 flexes.

In some examples in which only a portion of conductors 16 is coiled, core 18 may have a length (measured in a direction parallel to its longitudinal axis) that is substantially equal to (e.g., equal to or nearly equal to) length $_{LC}$ of the coiled section of conductor 16. Length $_{LC}$ of the coiled conductor portion 17 is the length of the coil defined by conductor 16, rather than the length of the conductor 16 required to define the coil (prior to defining the coil), and is measured in a direction substantially parallel to (e.g., nearly parallel or parallel to) longitudinal axis 15 (FIG. 2B) of lead 14. In other examples, core 18 may have a length that is less than or greater than the length $_{LC}$ of coiled portion 17 of conductors 16.

In some examples, an outer perimeter of core 18 defines the radius of curvature of the turns of coiled portion 17 of conductors 16. For example, during manufacture of lead 14, conductor 16 may be wrapped around core 18 to defined coiled portion 17, such that inner surface 20A defined by coiled portion 17 is directly adjacent to an outer surface of core 18.

In some examples, core 18 may be removed from lead 14 after lead 14 is implanted in the patient, e.g., after lead 14 has been introduced into the patient and guided through tissue until electrodes 22A, 22B of lead 14 are positioned at a target tissue site. In this way, core 18 may act as a stylet or guide wire that is used as an implant tool for implanting lead 14 in a patient. In order to further aid the implantation of lead 14 in the patient, the withdrawal of core 18 from the patient, core 18 may include a handle at its proximal end (which may remain outside of the patient even after lead 14 is implanted in the patient). The handle may have any suitable structure that enables a clinician to better grasp core 18.

In other examples, core 18 may not be used to implant lead 14 and conductor 16, or at least coiled portion 17 of conductor 16, may be sufficiently structurally rigid to enable lead 14 to be relatively easily manipulated by a clinician. And instead, lead 14 may define a hollow central lumen in place of core 18 during implantation of lead 14 in the patient. In these examples, coiled portion 17 of conductor 16 may be defined by, for example, wrapping conductor 16 around core 18 or another form, and subsequently removing core 18 from the inner lumen of coiled portion 16 or by wrapping conductor 16 around a form that defines an opening configured to receive a stylet.

Lead 14 includes coiled fixation element 24, which is defined by a plurality of turns of an elongated member 25. In the example shown in FIGS. 1-2B, coiled fixation element 24 and coiled portion 17 of conductors 16 are coaxial. At least one of the turns of fixation element 24 is configured to expand from a first dimension in a first state (e.g., a particular configuration or structure of fixation element 24) to a second dimension in a second state (e.g., another particular configuration or structure of fixation element 24). In this way, the profile of fixation element 24 may increase between the first and second states of fixation element 24. The dimension of fixation element 24 may be measured, for example, in a direction substantially perpendicular (e.g., perpendicular or nearly perpendicular) to longitudinal axis 15 (FIG. 2B) of lead 14. As discussed in further detail below, fixation element 24 may be configured to expand from the first dimension in the first state to the second dimension in the second state in response to the application of a threshold level of thermal energy. When lead 14 is implanted in a patient, the force applied against fixation element 24 by surrounding tissue may prevent fixation element 24 from expanding fully to the second dimension. However, fixation element 24 may still expand and may still configured to try to expand to the second dimension in the second state.

Each turn of fixation element 24 defines a loop of elongated member 25. The expansion of the one or more turns of fixation element 24, during the transition from the first state to the second state of fixation element 24, is in a direction away (e.g., radially outward) from coiled portion 17 of conductor 16, such that coiled fixation element 24 increases in size (e.g., the profile, such as the outer diameter, of the turns may increase) in the expanded state, in this way, coiled fixation element 24 is configured to expand in order to engage with surrounding tissue to help inhibit migration of lead 14 from an initial implant site. For example, fixation element 24 may engage with tissue in order to help inhibit migration of electrode 22 from a target stimulation site within the patient.

In some cases, elongated member 25 may be a wire, such as an electrically conductive wire. Elongated member 25 can comprise any suitable biocompatible material, such as, for example, a biocompatible shape memory material, such as Nitinol. A shape memory material is configured to remember an original shape and return to the original shape (from another shape) upon the application of thermal energy. As discussed in further details below, the original shape can be the second, expanded state of fixation element 24. In examples in which elongated member 25 comprises a shape memory material, thermal contact 23C can be directly or indirectly (e.g., via an intermediate layer) thermally connected to a proximal end or portion of elongated member 25. The contact 23C may define a part of a pathway for introducing thermal energy into elongated member 25 in order to cause expandable coiled fixation element 24 to expand from the first dimension in a first state to a second dimension in a second state. In some examples, the thermal energy is applied to elongated member 25 by applying electrical energy to elongated member 25 via contact 23C; the resistance in the material from which elongated member 25 is formed to the electrical energy generates the thermal energy. In this way, the thermal energy source that provides the thermal energy that causes fixation element 24 to expand from the first dimension to the second dimension may be an electrical energy source.

In the example shown in FIG. 1, coiled fixation element 24 is co-axially wound with conductors 16 and is located within coiled conductor portion 17. For example, elongated member 25 may be wrapped around core 18 (FIG. 2B) and coiled alongside conductors 16 to define coiled fixation element 24, such that in the first state, all of the turns of coiled fixation element 24 are adjacent turns of coiled portion 17 of conductors 16. In this way, coiled fixation element 24 may be wound within windings of conductors 16 and each of the turns (defined by windings of elongated member 25) may be interposed (e.g., positioned between) between adjacent windings of one or more conductors 16 within coiled portion 17. In some examples, the turns of fixation element 24 may be arranged in a helical pattern. Coiled fixation element 24 may be directly adjacent core 18 in the example shown in FIG. 1, or, in other examples, may be separated from core 18, e.g., by a sheath or the like wrapped around core 18.

In examples in which coiled fixation element 24 is wound within (e.g., between) windings of conductors 16 such that fixation element 24 is interposed with conductors 16, as shown in FIG. 1, coiled portion 17 of conductors 16 and coiled fixation element 24 may have substantially similar outer perimeters. For example, coiled fixation element 24 may be wound in alternating courses with conductors 16A, 16B, or in another interleaved pattern. By sizing coiled fixation element 24 to have substantially the same (e.g., the same or within about 10%) outer perimeter as coiled conductor portion 17, as shown in FIG. 1, the inclusion of coiled fixation element 24 in lead 14 may not contribute to the overall outer perimeter of lead 14, thereby minimizing the invasiveness of lead 14 attributable to the presence of fixation element 24. Thus, winding elongated member 25 within windings of conductors 16 may be useful for adding a fixation element 24 to lead 14 without increasing the invasiveness of lead 14.

Elongated member 25 can have any suitable length relative to conductor 16. A suitable length can be selected to be a length that enables a sufficient number of turns of coiled fixation element 24 to fix lead 14 to be defined. Ends of elongated member 25 are at any position relative to coiled conductor portion 17 suitable for defining coiled fixation element 24. In some examples, a proximal end of elongated member 25 is aligned with proximal end 14A of lead 14 (which may correspond to proximal ends of conductors 16 in some examples). However, in other examples, the proximal end of elongated member 25 may be positioned closer to coiled conductor portion 17 than proximal end 14A of lead 14. A distal end of elongated member 25 may terminate at a portion of lead 14 distal to coiled conductor portion 17, as shown in FIG. 1. For example, distal end 25B of elongated member 25 may be distal to coiled conductor portion 17 but proximal to electrodes 22, or distal to both coiled conductor portion 17 and electrodes 22. In other examples, the distal end of elongated member 25 may terminate proximal to the distal-most end of coiled conductor portion 17 or may be aligned with the distal-most end of coiled conductor portion 17.

In some examples, one or both ends of elongated member 25 are secured to coiled portion 17 in order to fix the relative position between coiled fixation element 24 and conductor 16. For example, one or both ends of elongated member 25 can be crimped, adhered, welded, or otherwise mechanically connected to conductor 16. In other examples, coiled fixation element 24 and conductor 16 remain sufficiently fixed relative to each other without the aid of a separate securing mechanism. For example, once coiled, elongated member retains its coiled shape as coiled fixation element 24, such that turns of conductor 16 hold turns of coiled fixation element 24 in place and limit movement of coiled fixation element 24 in a direction parallel to a longitudinal axis of lead. Core member 18 limits movement of coiled fixation element 24 in a direction perpendicular to a longitudinal axis of lead 14.

In the example shown in FIG. 1, coiled fixation element 24 is as tightly coiled as conductors 16 within coiled portion 17 of lead 14. For example, for every one turn of coiled fixation element 24, there may be one turn of each of the conductors 16. In other examples, however, coiled fixation element 24 and conductors 16 may have different relative densities of coils. For example, in some examples, coiled fixation element 24 may not be as tightly coiled as coiled conductors 16, e.g., for every two turns of each conductor 16, there may be one turn of coiled fixation element 24. As another example, conductors 16 may not be as tightly coiled as fixation element 24, e.g., for every two turns of elongated member 25, there may be one turn of conductors 16. Other relative densities are contemplated.

In some examples, as shown in FIG. 1, when fixation element 24 is in the first state, the turns of coiled portion 17 of conductor 16 and the turns of coiled fixation element 24 have substantially similar (e.g., identical or nearly identical) radii of curvature (e.g., measured in a cross section from an inner surface of the respective turn to longitudinal axis 15 of lead 14), the second state, as shown in FIGS. 2A and 2B, a subset of turns 24A-24J (some, but not all, of the turns) of coiled fixation element 24 extend away from coiled portion 17 of conductors 16, such that subset of turns 24A-24J of coiled fixation element 24 are no longer immediately adjacent turns of coiled portion 17 of conductors 16 and have different radii of curvature than turns of coiled portion 17.

FIG. 2A is a conceptual illustration of electrical stimulation lead 14 shown in FIG. 1, in which expandable coiled fixation element 24 is in a second state, which is also referred to herein as an expanded state. In the second state, turns 24A-24J have a different, larger dimension compared to coiled fixation element 24 in the first state (shown in FIG. 1).

FIG. 2B is a larger view of coiled fixation element 24 in the second state, and coiled conductor portion 17. As shown in FIG. 29, when coiled fixation element 24 is in the second state, turns 24A-24J extend away from coiled conductor portion 17, whereas other turns, such as turns 24K-24M of coiled fixation element 24 do not extend away from coiled conductor portion 17 to the same extent as turns 24A-24J. In the example shown in FIGS. 2A and 2B, turns 24K-24M do not expand and have the same radius of curvature in the first and second states of fixation element 24. In examples in which the turns of coiled fixation element have the same radius of curvature as conductors 16 within coiled portion 17 in the first state, turns 24K-24M have the same radius of curvature in the first or second states. In addition, in some examples, the proximal and distal ends of elongated member 25, from which coiled fixation element 24 is defined, stay in substantially the same position (e.g., nearly or completely the same position) in the first and second states of fixation element 24.

In the second state of coiled fixation element, turns 24A-24J of fixation element 24 extend away from coiled portion 17 of conductors 16 and are configured to engage with surrounding tissue to help fix lead 14 to surrounding tissue and help prevent lead 14 from migrating from a target stimulation site following implantation in the patient. Moreover, in the second state of fixation element 24, the turns 24A-24J of coiled fixation element 24 that extend away from coiled portion 17 define a relatively smooth, curvilinear surface that may not cause irritation to surrounding tissue. The curvilinear surfaces of expanded turns 24A-24J that engage with surrounding tissue help reduce tissue ingrowth around the expanded turns 24A-24J, which may help increase the ease with which lead 14 may be explanted from the patient. This may be useful if for example, lead 14 is a test lead. In comparison to some existing methods of fixing medical leads, such as suturing lead 14 to surrounding tissue, coiled fixation element 24 may permit implantation of lead 4 in a patient via a minimally invasive surgery, which may allow for reduced pain and discomfort for the patient, as well as a quicker recovery time.

Coiled fixation element 24 can have other configurations in other examples. For example, in some other examples, coiled fixation element 24 may be defined by a single turn of elongated member 25, and the single turn may expand away from coiled portion 17 of conductor 16 in the second state. In addition, in some other examples, in the first state, the turns of coiled fixation element 24 do not contact coiled portion 17 of conductors 16 when fixation element 24 is in the first state. In addition, in some other examples, the turns of coiled portion 17 of conductor 16 and fixation element 24 have different radii of curvature when fixation element 24 is in the first state. For example, the coils of fixation element 24 may have a greater radius of curvature than the coils of coiled portion 17 of conductor 16 and may, for example, wrap around at least a portion of coiled portion 17 of conductor 16. Other examples of coiled fixation element 24 in which coiled fixation element 24 is not coiled alongside conductor 16 and/or includes turns having a different radius of curvature than turns of coiled conductor 17 are described below with respect to FIGS. 3-5.

In the example shown in FIGS. 2A and 2B, one segment of consecutive turns 24A-24J of coiled fixation element 24 expand away from coiled portion 17 of conductors 16 in the second state of fixation element 24. In other examples, another arrangement of turns of coiled fixation element 24 may expand away from coiled portion 17 in the second state. For example, in another example, every other turn of coiled fixation element 24 for the entire length of coiled portion 17 or for a part of the length of coiled portion 17 may expand away from coiled portion 17 of conductors 16 in the second state. As another example, two segments of a plurality of consecutive turns of coiled fixation element 24 expand away from coiled portion 17 of conductors 16 in the second state of fixation element 24. The segments may be axially displaced from each other along longitudinal axis 15 of lead 14. For example, the segment of consecutive turns 24A-24J shown in FIGS. 2A and 2B may be a first segment of turns, and fixation element 24 may include a second segment of expandable turns closer to distal end 149 of lead 14, but still axially aligned with coiled portion 17 of conductors 16.

As discussed above, in some examples, such as when coiled fixation element 24 is formed from a shape memory material, coiled fixation element 24 is configured to expand upon application of a thermal energy to fixation element 24. For example, fixation element 24 may be formed from an electrically conductive elongated member 25, and, upon the application of electrical energy to a proximal end of elongated member 25 (e.g., contact 23C positioned at the proximal end), the electrical energy traverses through elongated member 25 to the at least one expandable turn of coiled fixation element 24, which expands away from coiled portion 17 of conductors 16 in response to the heat generated by the resistance in elongated member 25 to the electrical energy. The electrical energy can be, for example, an electrical current having an amplitude on the order of milliamps (mA). The current amplitude can be selected to not cause any physiologically significant stimulation of the patient's tissue. In some examples, the physiological significance can be indicated by perception of the stimulation by the patient, modulation of a nerve of the patient, elicitation of some motor response (e.g., a toe flexation or an anal sphincter contraction) from the patient, or any combination thereof. In some examples, the electrical energy that is used to cause expansion of fixation element 24 from the first dimension in the first state to the second dimension in the second state can be provided by electrical stimulator 12 or a separate device. In this way, a source of electrical energy may also be a thermal energy source.

In other examples, the thermal energy may be provided by, for example, body heat transferred to coiled fixation element 24 from tissue surrounding fixation element 24 when lead 14 (e.g., the entire lead or just a distal portion) is implanted in a patient.

Coiled fixation element 24 can have any suitable location relative to electrodes 22. For example, lead 14 may include one or more coiled fixation elements 24 proximal to electrodes 22, as shown in FIG. 1, distal to electrodes 22, or lead 14 may include more than one coiled fixation element (e.g., two fixation elements) that are located both proximal and distal to electrodes 22. In some examples, coiled fixation element 24 between electrodes 22 or both proximal and distal to electrodes 22 may help fix the portion of lead 14 comprising electrodes 22 to adjacent tissue, which may help better secure electrodes 22 at a target tissue site compared to a more proximal located fixation element 24.

When expandable fixation element 24 is in the first state in which the turns of expandable fixation element 24 are not expanded, lead 14 may assume a relatively low profile (e.g., a relatively small outer perimeter). The lower profile of lead 14 may permit it to be percutaneously implanted in a patient via an introducer (e.g., a needle), which may be less invasive than some proposed surgical implantation techniques, which may require introducing lead 14 through an incision. That is, in some examples, when fixation element 24 is in the first state, lead 14 is sized to be received in and traverse through a lumen of an introducer that is used to percutaneously implant at least a distal portion of lead 14 in a patient. The introducer may self-define an opening through skin of the patient to access the target stimulation site, and this self-defined opening may be less invasive than an incision. The introducer may be, for example, a needle, such as an 18, 19 or 20 gauge needle. The size of the introducer that is selected may depend upon the size of conductor 16, as well as upon the presence or absence of an outer jacket in which conductor 16 is positioned.

In the example shown in FIG. 1, electrical stimulator 12 includes processor 30, stimulation module 32, memory 34, power source 36, and telemetry module 38. In other examples, electrical stimulator 12 may include a fewer or greater number of components. Lead 14 is configured to be electrically coupled to stimulation module 32, such that stimulation module 32 can deliver electrical stimulation signals to a patient via electrodes 22 of lead 14. Proximal end 14A of lead 14 may be configured to be directly electrically and mechanically connected to electrical stimulator 12, as shown in FIG. 1, or to a lead extension that electrically and mechanically connects to electrical stimulator.

In general, electrical stimulator 12 comprises any suitable arrangement of hardware, alone or in combination with software and/or firmware, to perform the techniques attributed to electrical stimulator 12 and processor 30, stimulation module 32, and telemetry module 38. In various examples, processor 30 can include any one or more microprocessors, digital signal processors (DSPs), application specific integrated circuits (ASICs), field programmable gate arrays (FPGAs), or any other equivalent integrated or discrete logic circuitry, as well as any combinations of such components.

Electrical stimulator 12 may also include memory 34, which includes any volatile or non-volatile media, such as a random access memory (RAM), read only memory (ROM), non-volatile RAM (NVRAM), electrically erasable programmable ROM (EEPROM), flash memory, and the like. Memory 34 may store instructions for execution by processor 30. In some examples, memory 34 also stores one or more stimulation therapy programs that specify stimulation parameter values for the electrical stimulation therapy provided by electrical stimulator 12.

Although processor 30, stimulation module 32, and telemetry module 38 are described as separate modules, in some examples, processor 30, stimulation module 32, and telemetry module 38 can be functionally integrated. In some examples, processor 30, stimulation module 32, telemetry module 38 correspond to individual hardware units, such as ASICs, DSPs, FPGAs, or other hardware units.

Stimulation module 32 is configured to generate and deliver electrical stimulation to tissue of a patient via one or more electrodes 22 of lead 14. In some examples, processor 30 controls stimulation module 32 by selectively accessing and loading at least one stimulation therapy programs from memory 34 to stimulation module 32. In some cases, a clinician or patient may select a particular one of the stimulation therapy programs from a list using a medical device programming device (also referred to herein as a "programmer"). Processor 30 may receive the selection from the medical device programming device via telemetry module 38.

Stimulation module 32 is configured to generate and deliver stimulation therapy, i.e., electrical stimulation, according to stimulation parameters. In some examples, stimulation module 32 delivers therapy in the form of electrical pulses. In such examples, relevant stimulation parameters may include a voltage amplitude, a current amplitude, a pulse rate, a pulse width, a duty cycle, or the combination of electrodes of lead 14 with which stimulation module 32 delivers the stimulation signals to tissue of the patient. In other examples, stimulation module 32 delivers electrical stimulation in the form of continuous waveforms. In such examples, relevant stimulation parameters may include a voltage amplitude, a current amplitude, a frequency, a shape of the stimulation signal, a duty cycle of the stimulation signal, or the combination of electrodes with which stimulation module 32 delivers the stimulation signals to tissue of the patient.

Telemetry module 38 includes any suitable hardware, firmware, software or any combination thereof for communicating with another device, such as a medical device programming device. Processor 30 is configured to control telemetry module 38 to exchange information with the medical device programmer and/or another device external to electrical stimulator 12. Under the control of processor 30, telemetry module 38 may receive downlink telemetry, e.g., patient input, from and send uplink telemetry, e.g., an alert, to a programming device with the aid of an antenna, which may be internal and/or external to outer housing 40 of electrical stimulator 12. In some examples, electrical stimulator 12 may be configured to communicate with other devices, external to the patient or implanted in the patient, such as other electrical stimulators, control devices, or sensors, via telemetry module 38.

Power source 36 is configured to deliver operating power to the components of electrical stimulator 12. Power source 36 may include a battery and a power generation circuit to produce the operating power. In some examples, the battery may be rechargeable to allow extended operation.

Although not shown in FIG. 1, in some examples, therapy system 10 may also include a medical device programmer that is configured to program electrical stimulator 12. The programmer may be, for example, a dedicated or general purpose computing device (e.g., a handheld computing device or a workstation) that permits a clinician to program electrical stimulation therapy for delivery to a patient by electrical stimulator 12. For example, using the programmer, the clinician may specify electrical stimulation parameters for use by electrical stimulator 12 in the generation and delivery of electrical stimulation therapy, such as the voltage or current amplitude and frequency of the electrical stimulation signals generated by electrical stimulator 12 and delivered to the patient or the shape of the stimulation signal, the duty cycle of the stimulation signal, or the combination of electrodes of with which electrical stimulator 12 delivers stimulation to the patient. The medical device programmer may communicate with electrical stimulator 12 via cables or a wireless communication.

Therapy system 10 may be used to deliver electrical stimulation to any suitable target stimulation site in a patient. For example, the target stimulation site may be a tissue site proximate to a sacral nerve, an occipital nerve, or a tissue site proximate to any other suitable nerve, organ, muscle or muscle group in the patient, which may be selected based on, for example, the particular condition that therapy system 10 is implemented to address. For example, therapy system 10 may be used to deliver electrical stimulation therapy to a pudendal nerve, a perineal nerve or other areas of the nervous system, in which cases, lead 14 may be implanted and substantially fixed proximate to the respective nerve. As further examples, lead 14 may be positioned for temporary or chronic spinal cord stimulation for the treatment of pain, for peripheral neuropathy or post-operative pain mitigation, ilioinguinal nerve stimulation, intercostal nerve stimulation, gastric stimulation for the treatment of gastric mobility disorders and obesity, muscle stimulation (e.g., functional electrical stimulation (FES) of muscles), for mitigation of other peripheral and localized pain (e.g., leg pain or back pain), or for deep brain stimulation to treat mood or psychological disorders, movement disorders, and other neurological disorders.

Figure 3:
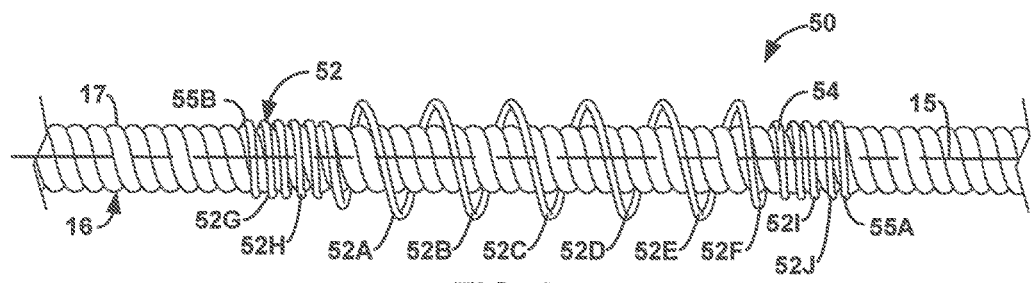
FIG. 3 is a conceptual illustration of a portion of an example electrical stimulation lead that includes an expandable coiled fixation element, which is coiled around a coiled conductor of the electrical stimulation lead.

FIG. 3 is a conceptual illustration of a part of an example electrical stimulation lead 50, which is similar to lead 14 of FIG. 1, but includes a different configuration of expandable coiled fixation element 52. As with lead 14, lead 50 includes conductor 16 and coiled portion 17 of conductor 16 is shown in FIG. 3. Rather than being coiled alongside conductor 16 as with elongated member 25 shown in FIG. 1, elongated member 54, from which coiled fixation element 52 is defined, is wrapped around a part of the outer surface of coiled portion 17 of conductor 16, e.g., elongated member 54 is disposed circumferentially about the outer surface of coiled conductor portion 17, to define a plurality of turns. Coiled fixation element 52 and coiled conductor portion 17 are coaxial in the example shown in FIG. 3. In some examples, coiled fixation element 52 is immediately adjacent coiled conductor portion 17. In other examples, coiled fixation element 24 is separated from coiled conductor portion 17 by a separator, such as a sheath that is positioned around all or part of coiled conductor portion 17.

In some examples, as shown in FIG. 3, elongated member 54 is wrapped only around a part of coiled conductor portion 17, such that coiled fixation element 52 only partially overlaps with coiled conductor portion 17. In other examples, elongated member 54 is wrapped around the entire coiled conductor portion 17, such that there is complete overlap between coiled conductor portion 17 and coiled fixation element 52. For example, proximal and distal portions of coiled conductor portion 17 may substantially align with (e.g., completely align with or generally align with) proximal and distal portions, respectively, of coiled fixation element 52.

In FIG. 3, coiled fixation element 52 is in the second, expanded state in which a subset of turns 52A-52F extends radially away from coiled portion 17 of conductor 16, while distal-most and proximal-most turns of coiled fixation element 52 remain unexpanded. In the second, expanded state, turns 52A-52F have a greater radius of curvature (e.g., measured from a center longitudinal axis 15 of lead 50 to the inner surface of the turn) than the nonexpandable turns of coiled fixation element, e.g., 52G-52J, and coiled conductor portion 17. In the first state, subset of turns 52A-52F is closer to coiled conductor portion 17 than in the second state. For example, in the first state, subset of turns 52A-52F may lie against coiled portion 17, e.g., as shown with respect to nonexpandable turns 52G-52J in FIG. 3.

In both the first and second states, coiled fixation element 52 defines at least part of an outer, exterior surface of lead 50 that contacts tissue of a patient when the portion of lead 50 including coiled fixation element 52 is implanted in the patient. In addition, in some examples, coiled conductor portion 17 also defines a part of the outer, exterior surface of lead 50.

In some examples, coiled fixation element 52 and conductors 16 remain sufficiently fixed relative to each other without the aid of a separate securing mechanism. For example, core member 18 may limit movement of coiled fixation element 52 in a direction perpendicular to longitudinal axis 15 of lead 14. In addition, in some examples, at least the proximal and/or distal non-expandable turns (e.g., turns 52G-52J) of coiled fixation element 52 may be more tightly coiled around coiled conductor portion 17 than the middle turns of coiled fixation element 52, which may help limit movement of coiled fixation element 52 in a direction parallel to longitudinal axis 15 of lead 50. As with elongated member 25 (FIG. 1), due to the properties of the material from which elongated member 54 is formed in some examples, elongated member 54 may be configured to retains its coiled shape once coiled, without the application of an uncoiling force.

In other examples, one or both ends 55A, 55B of coiled fixation element 52 may be secured to coiled conductor portion 17 in order to fix the relative position between coiled fixation element 52 and conductor 16. For example, one or both ends 55A, 55B of fixation element 52 of can be crimped, adhered, welded, or otherwise mechanically connected to conductor 16. As an example, a retainer ring can be positioned over ends one or both ends 55A, 55B of coiled fixation element 52 and around a part of coiled conductor portion 17 in order to secure coiled fixation element 52 to coiled conductor portion 17. The retainer ring can be formed from any suitable material, such as a metal or polymer, and can be attached to coiled fixation element 52 using any suitable technique, such as by adhering, welding or crimping the cap to coiled fixation element 52.

Figure 4:
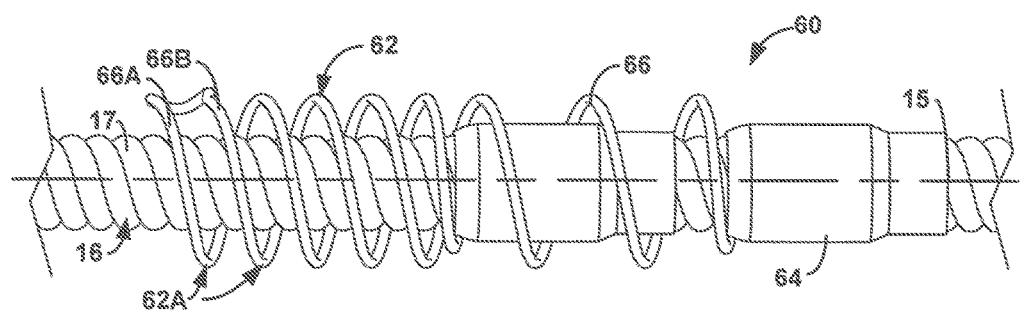
FIG. 4 is a conceptual illustration of a portion of another example electrical stimulation lead that includes an expandable coiled fixation element, which is coiled around coiled conductors of the electrical stimulation lead.

An example of lead 60 that includes expandable coiled fixation element 62 connected to coiled conductor portion 17 with a retainer ring 64 is shown in FIG. 4. As with expandable fixation element 52 (FIG. 3), fixation element 62 is disposed circumferentially about the outer surface of the coiled conductor portion 17. In the example shown in FIG. 4, only a proximal end of coiled fixation element 62 is mechanically fixed to coiled conductor portion 17 with retainer ring 64. Retainer ring 64 can be, for example, a metal or polymer shrink tube. As shown in FIG. 4, when a separate retainer ring 64 is used to fix expandable coiled fixation element 62 to coiled conductor portion 17, even the distal-most turns of fixation element 62 may expand to the second dimension in the second state without increasing the possibility of axial movement of fixation element 62 (in a direction substantially parallel to longitudinal axis 15 of lead 60) relative to coiled conductor portion 17.

In other examples of lead 60, a retainer ring can have another configuration, such as another position relative to fixation element 62. For example, a second retainer ring 64 can be positioned at distal end 62B of expandable coiled fixation element 62. In these examples, a middle portion of fixation element 62, which is positioned between proximal and distal ends of fixation element 62, expands from a first dimension in a first state to a second dimension in a second state. As another example, in some examples of lead 60, retainer ring 64 may be positioned to mechanically connect a distal end of fixation element 62 to coiled conductor portion 17, and a proximal end may be free to move, e.g., a turn of coiled fixation element 62 including the proximal end may be configured to expand from a first dimension in a first state to a second dimension in a second state. In another example, retainer ring 64 may be positioned to mechanically connect a middle portion of coiled fixation element 62 to coiled conductor portion 17, and distal and proximal ends of coiled fixation element 62 may be free to move, e.g., distal-most and proximal-most turns of coiled fixation element 62 may be configured to expand from a first dimension in a first state to a second dimension in a second state.

In the example shown in FIG. 4, elongated member 66 is positioned around an outer surface of coiled conductor portion 17 to define coiled fixation element 62. Coiled fixation element 62 is double stranded, such that for every turn of elongated member 66 around coiled conductor portion 17, there are two adjacent portions of elongated member 66. For example, as shown in FIG. 3, turn 62A of coiled fixation element 62 includes two adjacent portions 66A, 669 of elongated member 66.

Coiled fixation element 62 is configured to expand from a first dimension in a first state to a second dimension in a second state. In FIG. 4, coiled fixation element 62 is in the second, expanded state in which turns of coiled fixation element 62 extend radially away from coiled portion 17 of conductor 16. In the second, expanded state, turns of coiled fixation element 62 have a greater radius of curvature (e.g., measured from a center longitudinal axis of coiled fixation element 62, coiled conductor portion 17, or both, to the outer surface of the turn) than in the first state. For example, in the first state, turns of coiled fixation element 62 may lie against coiled portion 17.

In both the first and second states, coiled fixation element 62 defines at least part of an outer, exterior surface of lead 60 that contacts tissue of a patient when the portion of lead 60 including coiled fixation element 62 is implanted in the patient. In addition, in some examples, such as the one shown in FIG. 4, coiled conductor portion 17 also defines a part of the outer, exterior surface of lead 60.

Figure 5A:
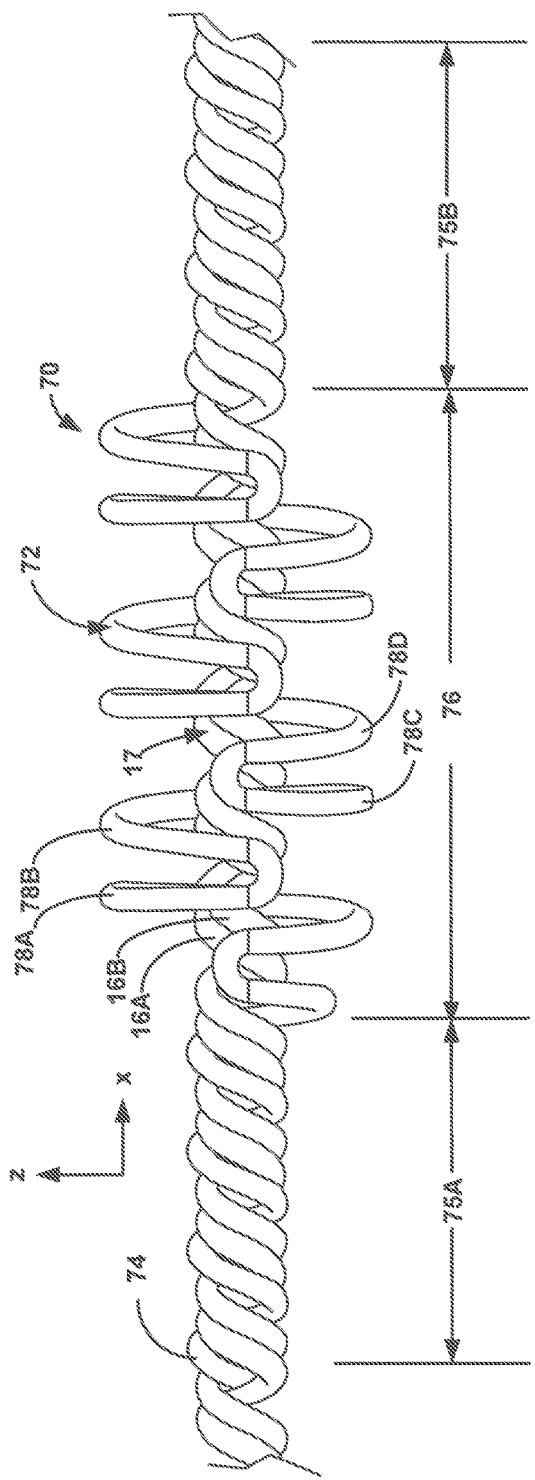
FIG. 5A is a conceptual illustration of a portion of an example electrical stimulation lead that includes an expandable coiled fixation element, which is coiled alongside conductors of the lead.

FIG. 5A is a conceptual illustration of a part of an example electrical stimulation lead 70, which is similar to lead 14 of FIG. 1, but includes an expandable coiled fixation element 72 that has a different configuration than expandable coiled fixation element 24. As with lead 14, lead 70 includes coiled conductors 16 and coiled portion 17 of conductor 16 is shown in FIG. 5A. Coiled fixation element 72 is defined by elongated member 74, which is coiled alongside coiled conductors 16A, 16B (e.g., as with elongated member 25 of lead 14) for part of the length (measured along the x-axis direction, where orthogonal x-z axes are shown in FIG. 5A for ease of description of the figure only) of lead 70, and is wrapped around a part of the outer surface of coiled portion 17 of conductor 16 (e.g., as with elongated members 54, 66 of leads 50, 60, respectively) for another part of the length of lead 70. In the example shown in HG 5A, elongated member 74 is coiled alongside coiled conductors 16A, 16B within segments 75A, 75B of lead 70 and wrapped around a part of the outer surface of coiled conductors 16A, 16B (and, therefore, coiled portion 17 of conductor 16) within segment 76 of lead 70. In the example shown in FIG. 5A, segment 76 is between segments 75A, 75B. In other examples, however, there may only be one segment 75A, 75B or more than one segment 76.

Within segments 75A, 75B of lead 70, elongated member 70 is coiled with conductors 16 in one direction and defines a portion of fixation element 72 that does not expand when coiled fixation element 72 expands from a first dimension in the first state to a second dimension in the second state. Coiled fixation element 72 and coiled conductor portion 17 are coaxial in the example shown in FIG. 5A. Within segments 75A, 75B, the outer surface of lead 70 that may contact tissue of a patient when lead 70 is implanted in the patient is defined by both elongated member 74, which is coiled to define coiled expandable fixation element 72, and conductors 16A, 16B.

In contrast to segments 75A, 75B of lead 70, within segment 76, elongated member 74 is wrapped around the outer surface of conductors 16 in more than one direction to define a portion of fixation element 72 that expands from the first dimension to the second dimension. Coiled fixation element 72 is shown in the expanded state in FIG. 5A. In some examples, an inner surface of coiled fixation element 72 is immediately adjacent an outer surface of coiled conductor portion 17 within segment 76. In other examples, the inner surface of coiled fixation element 72 is separated from the outer surface of coiled conductor portion 17 by a separator, such as a sheath that is positioned around all or part of coiled conductor portion 17.

Within segment 76, the outer surface of lead 70 that may contact tissue of a patient when lead 70 is implanted in the patient is defined by coiled expandable fixation element 72. For example, elongated member 74 may be disposed about the outer surface of conductors 16 to define a plurality of turns, including turns 78A-78D (collectively referred to as "turns 78"), as shown in FIG. 5A. However, elongated member 74 is not wrapped around conductors 16 in a single direction to define turns 78, such that turns 78 do not define a helical configuration, e.g., as some examples of turns of coiled fixation element 24 may define (FIG. 2A, 2B). Instead, within segment 76, elongated member 74 is wrapped around conductors 16 in two directions to define noncontinuous turns of expandable coiled fixation element 72. The noncontinuous turns of expandable coiled fixation element 72 may be useful for, for example, dislodging lead 70 from tissue ingrowth because the tissue may find a straight path through coiled fixation element 72.

In the example shown in FIG. 5A, elongated member 74 is wrapped around the outer surface of conductors 16 in a first circumferential direction to define one turn 78A, and then member 74 is wrapped back around the outer surface of conductors 16 in a second circumferential direction that is opposite to the first direction to define another turn 78B. Thereafter, member 74 is wrapped around the outer surface of conductors 16 in the first circumferential direction to define turn 78C, and subsequently wrapped back around the outer surface of conductors 16 in the second circumferential direction that is opposite to the first direction to define another turn 78D. This wrapping of elongated member 74 in alternating directions may continue for as many turns as desired, which may be selected based on the desired length (measured in a direction parallel to a longitudinal axis of lead 70) of the expanded portion of coiled expandable fixation element 72. In addition, any pattern of wrapping in the first and second circumferential directions may be used instead of or in addition to, the alternating pattern shown in FIG. 5A.

In FIG. 5A, coiled fixation element 72 is in the second, expanded state in which a subset of turns (including turns 78A-78D) extend radially away from coiled portion 17 of conductor 16, while distal-most and proximal-most turns of coiled fixation element 72 remain unexpanded. In the second, expanded state, the expanded turns have a greater radius of curvature than the nonexpandable turns of coiled fixation element 72. In the first state, the subset of turns that expand is closer to coiled conductor portion 17 than in the second state. For example, in the first state, subset of turns 78A-78D and the other expanded turns may sit against coiled portion 17.

In the second, expanded state shown in FIG. 5A, turns 78 may have any suitable dimension relative to each other. In some examples, all of the turns 78 may have the same dimensions in the x-axis, z-axis, and y-axis dimensions. In other examples, at least two turns 78 may have different dimensions in one, two, or all three of the x-axis, z-axis, and y-axis dimensions. Turns 78 of different dimensions may help increase variability of tissue with which coiled fixation element 72 may engage with in order to help fix electrodes 22A, 22B at a target tissue site.

In some examples, coiled fixation element 72 and conductors 16 remain sufficiently fixed relative to each other without the aid of a separate securing mechanism. For example, the wrapping of elongated member 74 and conductors 16 together may help fix the relative position of an inner surface of.

Figure 5B:
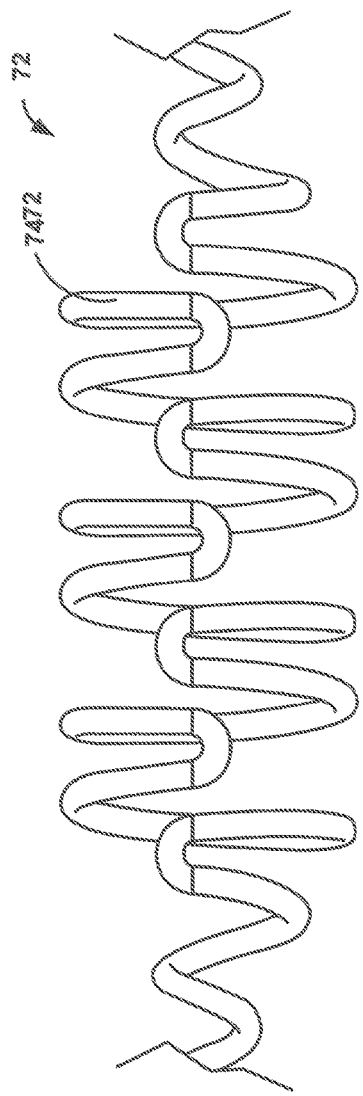
FIG. 5B is a conceptual illustration of the expandable coiled fixation element shown in FIG. 5A.

FIG. 5B is an illustration of coiled expandable fixation element 72 of lead 70 of FIG. 5A, and illustrates the wrapping of elongated member 74 in different directions to define turns of fixation element 72 that expand away from conductors 16 in the second state of fixation element 72.

In some examples, a portion of conductors 16 that extends through the section of lead 70 with coiled fixation element 72 may be uncoiled, e.g., may be relatively straight. For example, rather than wrapping around coiled conductor portion 17, as shown in FIG. 5A, coiled fixation element 72 may wrap around un-coiled (e.g., substantially straight) conductors 16. This may help reduce the outer perimeter of lead 70 through the portion with coiled fixation element 72 because conductors 16 may have a smaller profile (e.g., smaller outer perimeter) when uncoiled. In some examples in which a portion of conductors 16 that extends through the section of lead 70 with coiled fixation element 72 is uncoiled, when coiled fixation element 72 is in the first, non-expanded state, coiled fixation element 72 may not protrude past the outer surface of lead 70 defined by portions of conductor 16 distal and proximal to coiled fixation element 72. In some examples, the uncoiled portion may be positioned between, for example, two coiled sections of conductors 16 to which coiled fixation element 72 may be mechanically connected, such that when a clinician pulls on a proximal end of lead 70, conductors 16 elongate and decrease a profile of an expanded coiled fixation element 72.

Figure 6A:
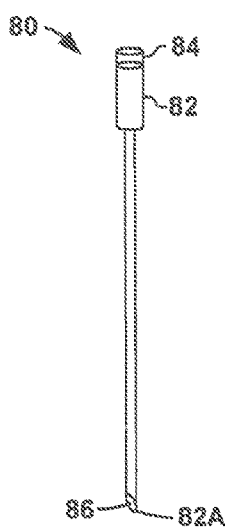
FIG. 6A is a conceptual illustration of an example introducer assembly that includes an introducer needle and a stylet.
Figure 6B:
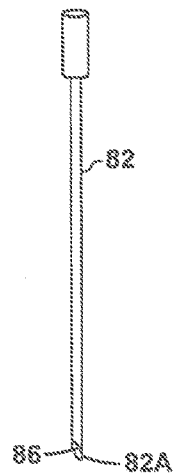
FIG. 6B is a conceptual illustration of an example introducer needle of the introducer assembly of FIG. 6A.
Figure 6C:
FIG. 6C is a conceptual illustration of an example stylet of the introducer assembly of FIG. 6A.

As discussed above, in some examples, a lead that includes an expandable coiled fixation element that defines a part of the outer surface of the lead can be percutaneously implanted in a patient with the aid of an introducer. The introducer may be configured to define a pathway from an entry point in the skin of the patient to a target stimulation site for the electrodes of the lead. FIG. 6A illustrates an example introducer assembly 80, which includes introducer needle 82 and stylet 84, which is disposed inside of lumen 86 defined by introducer needle 82. FIG. 6B illustrates introducer needle 82 and FIG. 6C illustrates stylet 84. While FIGS. 6A-6C are described with respect to lead 14 (FIG. 1), in other examples, introducer assembly 80 may be used to implant any lead including an expandable coiled fixation element in a patient.

Needle 82 includes a pointed tip 82A that helps define a pathway through tissue of the patient as needle 82 is guided through the tissue. In some examples, the pointed tip 82A of needle 82 is sharp enough to define a percutaneous opening, e.g., without the aid of a previously defined incision, for needle 82. Stylet 84 may be disposed inside of introducer needle 82 as needle 82 is introduced into the patient in order to help prevent coring of tissue by needle 82 as needle 82 is advanced through tissue. In other examples, however, an introducer that is used to implant lead 14 may not include stylet 84. For example, only introducer needle 82 may be introduced into the patient in order to define a pathway through tissue of the patient.

Lumen 86 of needle 82 is configured to receive lead 14 including expandable coiled fixation element 24. In some examples, needle 82 is configured such that lumen 86 is sized to receive lead 14 while expandable fixation element 24 is in the first state, i.e., prior to expansion of expandable fixation element 24 to the second dimension in the second state. In some cases, the inner surface of needle 82 that defines lumen 86 may interact with expandable fixation element 24 to help retain the first state of expandable fixation element 24.

Figure 7:
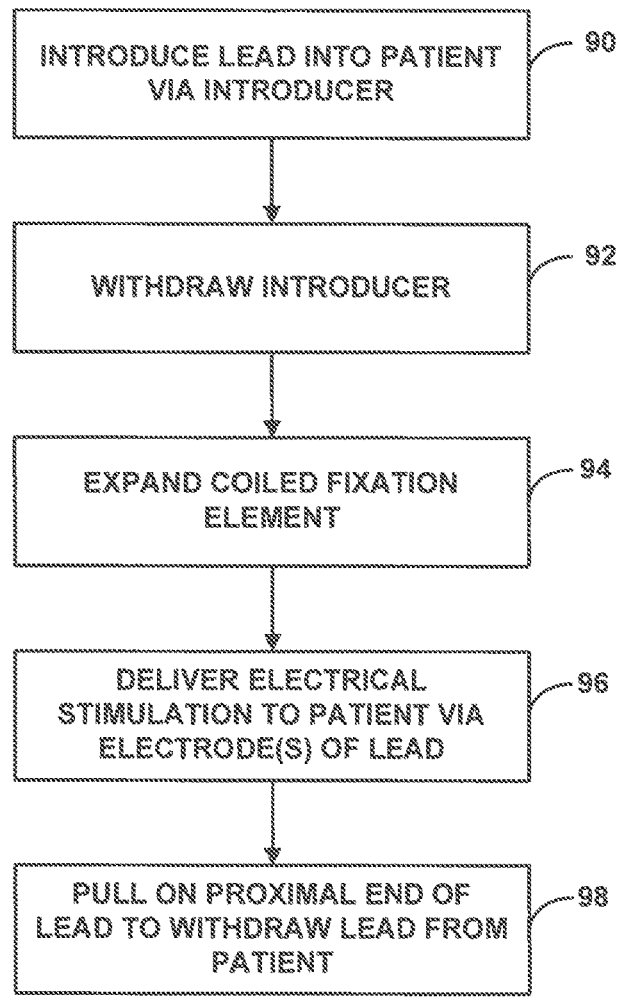
FIG. 7 is a flow diagram of an example technique for introducing an electrical stimulation lead that includes an expandable coiled fixation element, and subsequently withdrawing the electrical stimulation lead from the patient.

FIG. 7 is a flow diagram illustrating an example technique for implanting a lead that includes an expandable coiled fixation element that defines a part of the outer surface of the lead in a patient. While FIG. 7 is described with respect to lead 14 shown in FIG. 1, in other examples, the technique shown in FIG. 7 can be used to implant other leads, such as lead 50 (FIG. 3), lead 60 (FIG. 4) or other leads. In addition, while FIG. 7 is described with reference to introducer assembly 80 of FIG. 6A, in other examples, other introducer assemblies can be used to implant a lead including an expandable coiled fixation element. In addition, if desired, a surgical technique that includes implanting lead 14 through an incision in the patient may also be used, if desired. However, an introducer assembly may be less invasive than the surgical techniques using an incision.

In accordance with the example technique shown in FIG. 7, introducer assembly 80 is introduced into tissue of a patient and a distal end (which includes pointed tip 82A) of needle 82 is guided to target stimulation site within the patient (90). In some examples, the target stimulation site is a tissue site that is proximate the target nerve to be modulated by the electrical stimulation therapy delivered via electrodes 22 of lead 14. Introducer assembly 80 may be inserted into the patient percutaneously or via an incision. Needle 82 defines a pathway through tissue of the patient from an entry point in the skin of the patient to the target stimulation site. Prior to, after, or as introducer assembly 80 is guided to the target stimulation site, lead 14 is introduced into lumen 86 of needle 82 (92). In particular, distal end 14B of lead 14 is introduced into lumen 86 before proximal end 14A. If stylet 84 is positioned in lumen 86, stylet 84 may be removed from lumen 86 prior to introduction of lead 14 into lumen 86.

Lead 14 is advanced through lumen 86 of needle 82 until electrodes 22 adjacent to distal end 14B of lead 14 are positioned proximate to the target stimulation site. Positioning of introducer needle 82 and/or lead 14 may be aided by imaging techniques, such as by fluoroscopy using markers (e.g. radio-opaque or otherwise visible) on lead 14 or using ultrasound. The markers may also help indicate a location of coiled fixation element 24 with respect to one or more points of introducer needle 82 (e.g., tip 82A of needle 82). Distal end 14B of lead 14 may be advanced through lumen 86 of needle 82 until at least distal end 14B protrudes past tip 82A of needle 82 and into tissue of the patient and expandable fixation element 24 is deployed from needle 82 (i.e., is advanced past tip 82A of needle 82). In other examples, expandable fixation element 24 may be deployed from needle 82 by withdrawing needle 82 (in a direction away from the patient), thereby exposing lead 14. In either example, after electrodes 22 of lead 14 are at the target stimulation site, introducer needle 82 may be withdrawn from the patient, leaving lead 14 at least partially within the patient.

As discussed above, proximal end 14A of lead 14 may be electrically and mechanically connected to electrical stimulator 12, which may be carried external to the patient or implanted in the patient. In some examples, after lead 14 is at the target stimulation site and introducer needle 82 is withdrawn (92), proximal end 14A of lead 14 remains outside of the patient and may be electrically and mechanically connected to an external electrical stimulator 12. In other examples, after lead 14 is at the target stimulation site and introducer needle 82 is withdrawn (92), proximal end 14A of lead may be implanted in the patient and may be electrically and mechanically connected to an implanted electrical stimulator 12.

In accordance with the technique shown in FIG. 7, coiled fixation element 24 is expanded from a first dimension in the first state to the second dimension in a second state (94). In some examples, coiled fixation element 24 may be expanded to the second state before introducer needle 82 is withdrawn (92), while in other examples, coiled fixation element 24 may be expanded after introducer needle is withdrawn (92). Expanding coiled fixation element 24 prior to complete withdrawal of needle 82 from the patient, but after deployment of fixation element 24 from lumen 86, may help fix the position of lead 14 during withdrawal of needle 82 from the patient, which may generate tugging and pulling forces along lead 14 in an axial direction (e.g., along longitudinal axis 15).

In some examples, immediately upon deployment into body tissue, coiled fixation element 24 remains in the first state, in which turns of fixation element 24 do not extend away from coiled conductor portion 17. In these examples, in order to expand coiled fixation element 24 into the second state (94), thermal energy is applied to coiled fixation element 24. In the case of coiled fixation element 24 comprised of a shape memory material, the thermal energy may be sufficient to bring coiled fixation element 24 to a temperature greater than or equal to its transition temperature for changing shape, which is described in further detail below with reference to FIG. 8. As discussed above, thermal energy may be applied to coiled fixation element 24 by applying electrical energy (e.g., electrical current) to elongated member 25; in this example, the resistance in the material from which member 25 is formed to the electrical energy generates the thermal energy.

In one example, elongated member 25 is electrically conductive, and upon the application of electrical energy to a contact 23A near the proximal end of elongated member 25, the electrical energy traverses through elongated member 25 to the at least one expandable turn of coiled fixation element 24, which expands away from coiled portion 17 in response to the heat generated by the electrical energy. In some examples, electrical stimulator 12 is electrically connected to elongated member 25 and provides the electrical energy that generates the thermal energy that causes coiled fixation element 24 to expand from the first dimension in the first state (e.g., as shown in FIG. 1) to the second dimension in the second state (e.g., as shown in FIGS. 2A and 2B). In other examples, a device with an electrical energy source separate from electrical stimulator 12 is electrically connected to elongated member 25 and provides the electrical energy that generates the thermal energy that causes coiled fixation element 24 to expand.

Regardless of the source of electrical energy, the current provided to elongated member 25 to cause expansion of coiled fixation element 24 from the first state to the second state may be less than about 12.5 mA, such as a current in a range of about 1 mA to about 12.5 mA. In some examples, the energy level may be selected so as to not activate any physiological response from the patient, and may be selected to be under a perception threshold of the patient.

In another example, in order to expand coiled fixation element 24 into the second state (94), body heat from tissue surrounding coiled fixation element 24 provides the thermal energy that causes coiled fixation element 24 to expand from the first state to the second state. For example, elongated member 25 may be comprised of a shape memory material that is configured to revert to shape of the second state (e.g., in which at least one turn extends away from coiled conductor portion 17) upon exposure to a temperature of about 33.2° C. to about 38.2° C. (about 92° F.-to about 101° F.), such as about 34.4° C.-to about 37.8° C. (about 94° F.-to about 100° F.), or about 35.4° C.-to about 37.8° C. (about 96° F.-to about 100° F.).

In the second state, at least one of the turns of coiled fixation element 24 extends away from coiled conductor portion 17 (e.g., radially away from coiled conductor portion 17), such that, when lead 14 is implanted in tissue of the patient, the expanded turns of coiled fixation element 24 engage with surrounding tissue to substantially fix electrodes 22 proximate to the stimulation target site. In some examples, two or more of the turns of fixation element 24 extends away from coiled conductor portion 17 in the second state, and, in other examples, all of the turns of fixation element 24 extends away from coiled conductor portion 17 in the second state.

In some examples in which lead 14 includes core 18, after coiled fixation element 24 is expanded to increase its profile (94), core 18 may be removed from lead 14 and from the patient. For example, a clinician may pull on a proximal end of core 18 (e.g., that remains outside of the patient) and pull the proximal end of core 18 in a direction away from the patient. As discussed above, core 18 may provide structural rigidity to lead 14, e.g., to enable a clinician to better manipulate lead 14 during implantation of lead 14 in the patient. Flexibility of lead 14 imparted to lead 14 after removal of core 18 may be more comfortable to the patient in some examples. Thus, in some examples, it may be desirable to remove core 18 after lead 14 is implanted in the patient.

In accordance with the technique shown in FIG. 7, after lead 14 is substantially secured in place with the aid of coiled fixation element 24 in the second, expanded position, electrical stimulator 12 may deliver electrical stimulation to the patient via electrodes 22 of lead 14 (96). As discussed above, the stimulation may be, in some examples, electrical stimulation that is delivered on a trial, temporary basis in order to evaluate the efficacy of the electrical stimulation therapy. In other examples, the stimulation delivered by electrical stimulator 12 via lead 14 may be chronic, long-term stimulation (e.g., on the order of months or years).

Upon determination, e.g., by a clinician, that lead 14 should be explanted from the patient, the clinician, manually or with the aid of a device, may withdraw lead 14 from patient. In the technique shown in FIG. 7, the clinician pulls on proximal end 14A of lead 14 to withdraw lead 14 from the patient (98). Due to the coiled nature of coiled fixation element 24 and coiled conductor portion 17 around which coiled fixation element 24 is positioned, pulling on proximal end 14A of lead 14 may elongate coiled conductor portion 17 of lead 14 along longitudinal axis 15, thereby causing coiled fixation element 24 to contract towards coiled fixation element 17. When coiled fixation element 24 contracts towards coiled conductor portion 17, coiled fixation element 24 may contract towards the first state and at least partially disengage with surrounding tissue. At least partially disengaging coiled fixation element 24 from surrounding tissue may help reduce the extent to which coiled fixation element 24 fixes lead 14 in place. In this way, lead 14 may be configured to aid explanation of lead 14 from patient 14.

When proximal end 14A of lead 14 is pulled to cause coiled fixation element 24 to contract towards coiled fixation element 17, coiled fixation element 24 may contract back to the first state. However, in other examples, coiled fixation element 24 may contract from the second state towards the first state (in which the turns of coiled fixation element 24 are closer to coiled conductor portion 17), but may not completely return back to the first state (e.g., may not have the same turn radius as coiled conductor portion 17 in the case of lead 14 or may not completely lie against coiled conductor portion 17 in the case of leads 50, 60).

The order of steps shown in FIG. 7 is merely one example of a method of implanting a lead including an expandable coiled fixation element. In other examples, the steps may be performed in a different order.

As discussed above, in some examples, an expandable coiled fixation element of a medical lead is formed from a shape memory material. A shape memory material may be, for example, a shape memory alloy, which may also be referred to as a smart metal, memory metal, memory alloy, or smart alloy. In one example, an expandable coiled fixation element described herein is formed from a nickel titanium (NiTi) shape memory alloy. The shape memory material selected for the expandable coiled fixation element may have a one-way memory effect in some examples. With a one-way memory effect shape memory material, a material may remember one shape, which may be referred to as its original shape. The memory may be deformed from its original shape to a second shape while the material is in a cold state (e.g., a temperature below the transition temperature of the material). The material will retain the second shape until it is heated above the transition temperature of the material. In response to being heated to the transition temperature of the material, the material will revert back to its original shape. Once the material cools after heating to the transition temperature, the material will retain the original shape until deformed again. The original shape may, for example, define the coiled fixation element in the second, expanded state, and the second shape may, for example, define the coiled fixation element in the first state.

In another example, the shape memory material selected for the expandable coiled fixation element may have a two-way memory effect. With a two-way memory effect shape memory material, the material may remember two different shapes: a first shape at a first temperature (or a first range of temperatures) and a second shape at a second temperature (or a second range of temperatures). With a two-way memory effect shape memory material, the material may be deformed in a cold state (e.g., a temperature below the first temperature or range of temperatures), and will retain the deformed shape until it is heated above the first transition temperature of the material. At the first transition temperature, the material may revert to the first shape. Once the material cools after heating, the material will retain its first shape until deformed again or until heated to the second transition temperature, at which time, the material may revert to the second shape. Once the material cools after heating, the material will retain its second shape until a force is applied to further deform the material.

Figure 8:
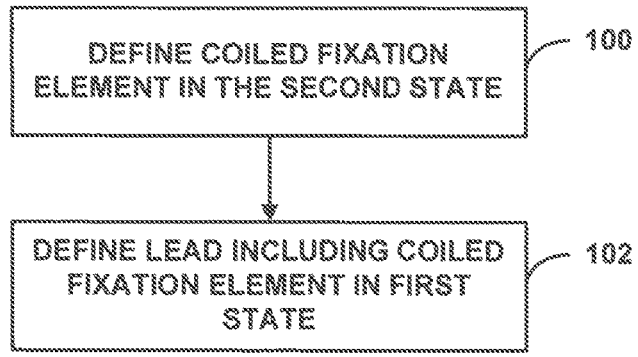
FIG. 8 is a flow diagram of an example technique for forming an expandable coiled fixation element from a shape memory material.

FIG. 8 is a flow diagram of an example technique for forming an expandable coiled fixation element of a medical lead. While FIG. 8 is described with respect to lead 14 shown in FIG. 1, in other examples, the technique shown in FIG. 8 can be used to form coiled fixation elements of other leads, such as lead 50 (FIG. 3), lead 60 (FIG. 4) or other leads.

In accordance with the technique shown in FIG. 8, while elongated member 25 is at or above the transition temperature of the shape memory material from which elongated member 25 is formed, elongated member 25 is manipulated to define coiled fixation element 24 in the second state in which coiled fixation element 24 has the second dimension (100). Elongated member 25 may be coiled manually or with the aid of a semi-automated or automated device.

After coiling elongated member 25 to define coiled fixation element 24 having the second dimension in the second state (100), elongated member 25 may be deformed (e.g., straightened) and coiled with conductors 16 to define lead 14 that may look like lead 14 shown in FIG. 1, in which coiled fixation element 24 is in the first state (102). For example, elongated member 25 can placed adjacent to conductor 16 and both elongated member 25 and conductor 16 can be wrapped around core 18. In some examples, core 18 remains within the lumen defined by the coiled fixation element 24 defined by elongated member 25 and coiled conductor portion 17 when lead 14 is implanted in a patient. In other examples, core 18 may be removed from the lumen after the coil defined by elongated member 25 and conductor 16 are formed. After defining lead 14 including coiled fixation element 24 in the first state, lead 14 may be implanted in the patient while coiled fixation element 24 is in the first state.

In other examples, after defining a coiled fixation element in the second state with an elongated member, the elongated member can be subsequently coiled around coiled conductor portion 17 to define the coiled fixation element in the first state. Examples of such coiled fixation elements are described above with respect to coiled fixation elements 52, 66, and 72 of FIGS. 3-5, respectively.

Various examples have been described. These and other examples are within the scope of the following claims.

What is claimed is:

1. A system comprising:
a medical lead defining a longitudinal axis, the medical lead comprising:
a coiled conductor that defines at least part of an outermost surface of the medical lead;
an electrode electrically connected to the coiled conductor; and
an expandable coiled fixation element that defines at least part of the outermost surface of the medical lead, the expandable coiled fixation element defining a plurality of turns, and at least one of the turns being configured to expand away from the coiled conductor from a first dimension in a first state to a second dimension in a second state, wherein the first and second dimensions are measured in a direction substantially perpendicular to the longitudinal axis.

2. The system of claim 1, further comprising a core member, wherein the coiled conductor and the expandable coiled fixation element are wrapped around the core member.

3. The system of claim 1, wherein the electrode is defined by an exposed electrically conductive portion of the coiled conductor.

4. The system of claim 1, wherein the electrode comprises an electrically conductive collar electrically connected to the coiled conductor.

5. The system of claim 1, wherein the turns of the plurality of turns of the expandable coiled fixation element are interposed between turns of the coiled conductor.

6. The system of claim 1, wherein the expandable coiled fixation element is coiled around the coiled conductor.

7. The system of claim 1, wherein radii of curvature of a first turn of the coiled conductor and a second turn of the expandable coiled fixation element are substantially similar.

8. The system of claim 1, wherein radii of curvature of turns of the coiled conductor and turns of the expandable coiled fixation element are different.

9. The system of claim 1, wherein the expandable coiled fixation element comprises a first end at a first position relative to the coiled conductor and a second end at a second position relative to the coiled conductor, wherein the first and second ends remain at the first and second positions, respectively, when the at least one of the turns is in the first and second states.

10. The system of claim 1, further comprising an electrical stimulator configured to be located external to a patient, wherein the coiled conductor is configured to electrically connect the electrode to the electrical stimulator.

11. The system of claim 1, wherein the expandable coiled fixation element comprises a shape memory material that is configured to expand from the first dimension in the first state to the second dimension in the second state upon application of thermal energy to the shape memory material.

12. The system of claim 1, further comprising an electrical energy source configured to generate electrical current, wherein the expandable coiled fixation element is configured to electrically connect to the electrical energy source, the at least one turn of the expandable coiled fixation element being configured to expand away from the coiled conductor upon application of the electrical energy to the expandable coiled fixation element by the electrical energy source.

13. The system of claim 1, wherein the coiled conductor comprises an electrically conductive member surrounded by electrical insulation.

14. A medical lead defining a longitudinal axis, the medical lead comprising:
means for conducting electrical stimulation signals, wherein the means for conducting electrical stimulation signals comprises a coiled portion defining at least part of an outermost surface of the medical lead;

means for generating electrical stimulation therapy, wherein the means for generating electrical stimulation therapy is electrically connected to the means for conducting electrical stimulation signals; and means for fixing the means for conducting electrical stimulation signals to tissue of a patient, the means for fixing being coiled and defining at least part of the outermost surface of the medical lead, the means for fixing defining a plurality of turns and at least one of the turns being configured to expand away from the coiled portion of the means for conducting from a first dimension in a first state to a second dimension in a second state, wherein the first and second dimensions are measured in a direction substantially perpendicular to the longitudinal axis.

15. The medical lead of claim 14, wherein the means for fixing comprises a shape memory material.

16. The medical lead of claim 14, wherein the turns of the plurality of turns of the means for fixing are interposed between turns of the coiled portion of the means for conducting.

17. The medical lead of claim 14, wherein the means for fixing is coiled around the means for conducting.

18. The medical lead of claim 14, wherein the means for conducting electrical stimulation signals comprises an electrically conductive member surrounded by means for electrically insulating the electrically conductive member.

19. A method comprising:
implanting a medical lead in a patient, the medical lead defining a longitudinal axis, the medical lead comprising:
a coiled conductor that defines at least part of an outermost surface of the medical lead;
an electrode electrically connected to the coiled conductor; and
an expandable coiled fixation element that defines at least part of the outermost surface of the medical lead, the expandable coiled fixation element defining a plurality of turns, and at least one of the turns being configured to expand away from the coiled conductor from a first dimension in a first state to a second dimension in a second state wherein the first and second dimensions are measured in a direction substantially perpendicular to the longitudinal axis; and
applying electrical energy to the expandable coiled fixation element via an electrical energy source to cause the expandable coiled fixation element to expand away from the coiled conductor.

20. The method of claim 19, wherein the electrical energy source comprises an electrical stimulator that is configured to deliver electrical stimulation signals via the coiled conductor and the electrode of the medical lead.

21. The method for claim 20, further comprising electrically connecting the coiled conductor to the electrical stimulator and controlling the electrical stimulator to deliver electrical stimulation therapy to the patient via the electrode of the medical lead.

22. The method of claim 19, wherein the turns of the plurality of turns of the expandable coiled fixation element are interposed between turns of the coiled conductor.

23. The method of claim 19, wherein the expandable coiled fixation element is coiled around the coiled conductor.

24. The method of claim 19, wherein the coiled conductor comprises an electrically conductive member surrounded by electrical insulation.

25. A method comprising:
coiling a conductor to define a coiled conductor portion that defines at least part of an outermost surface of a medical lead, the medical lead defining a longitudinal axis; and
coiling an elongated member to define an expandable coiled fixation element that defines at least part of the outermost surface of the medical lead, the expandable coiled fixation element being configured to expand away from the coiled conductor from a first dimension in a first state to a second dimension in a second state, wherein the first and second dimensions are measured in a direction substantially perpendicular to the longitudinal axis.

26. The method of claim 25, wherein coiling the conductor and coiling the elongated member comprises coiling the conductor and the elongated member around a core member.

27. The method of claim 25, wherein coiling the elongated member comprises coiling the elongated member such that the elongated member defines a plurality of turns that are interposed between turns of the coiled conductor portion.

28. The method of claim 25, wherein coiling the elongated member comprises coiling the elongated member around the coiled conductor portion.

29. The method of claim 25, wherein the elongated member comprises a shape memory material, and wherein coiling the elongated member comprises:
while the elongated member is at a first temperature, defining the expandable coiled fixation element in the second state; and
while the expandable coiled fixation element is at a second temperature, shaping the expandable coiled fixation element to define the coiled fixation element in the first state.

30. The method of claim 25, wherein the coiled conductor comprises an electrically conductive member surrounded by electrical insulation.

31. The system of claim 1, the expandable coiled fixation element and at least a portion of the coiled conductor being coaxial.

32. The system of claim 1, wherein the plurality of turns includes a first plurality of turns, and wherein the coiled conductor defines a second plurality of turns.

33. The system of claim 32, wherein each turn of the second plurality of turns defines a portion of the at least part of the outermost surface of the medical lead.

* * * * *